United States Patent
Chen et al.

(10) Patent No.: US 7,829,731 B2
(45) Date of Patent: Nov. 9, 2010

(54) METHYLHYDROXYLAMINOPROPANOL DERIVATIVE AND ITS USE AS INTERMEDIATE FOR PREPARATION OF 3-METHYLAMINO-1-(2-THIENYL)PROPAN-1-OL

(75) Inventors: Bo-Fong Chen, Taoyuan (TW); Jinun-Ban Yeh, Taoyuan (TW); Weichyun Wong, Taoyuan (TW)

(73) Assignee: SCI Pharmtech, Inc., Taoyuan (TW)

( * ) Notice: Subject to any disclaimer, the term of this patent is extended or adjusted under 35 U.S.C. 154(b) by 320 days.

(21) Appl. No.: 11/926,772

(22) Filed: Oct. 29, 2007

(65) Prior Publication Data

US 2009/0112000 A1    Apr. 30, 2009

(51) Int. Cl.
   *C07D 333/12* (2006.01)
(52) U.S. Cl. ...................................................... 549/75
(58) Field of Classification Search .................... 549/75
   See application file for complete search history.

(56) References Cited

U.S. PATENT DOCUMENTS

| 7,259,264 B2 | 8/2007 | Sturmer |
| 2008/0171887 A1 | 7/2008 | Pospisilik et al. |

FOREIGN PATENT DOCUMENTS

| WO | 2008/077645 A1 | 7/2008 |

*Primary Examiner*—Taylor Victor Oh
(74) *Attorney, Agent, or Firm*—Sughrue Mion, PLLC

(57) ABSTRACT

The present invention provides a methylhydroxylaminopropanol derivative and the methylhydroxylaminopropanol derivative of the present invention is used as an intermediate for preparation of 3-methylamino-1-(2-thienyl)propan-1-ol, which is an intermediate for preparation of (+)-(S)—N-methyl-3-methyl-3-(1-naphthyloxy)-3-(2-thienyl)propylamine oxalate. The present invention also provides a process for preparing 3-methylamino-1-(2-thienyl)propan-1-ol with higher yield and lower cost, wherein the methylhydroxylaminopropanol derivative is used as an intermediate.

16 Claims, No Drawings

METHYLHYDROXYLAMINOPROPANOL DERIVATIVE AND ITS USE AS INTERMEDIATE FOR PREPARATION OF 3-METHYLAMINO-1-(2-THIENYL)PROPAN-1-OL

BACKGROUND OF THE INVENTION

1. Field of the Invention

The present invention relates to a novel methylhydroxylaminopropanol derivative and its use as an intermediate for preparation of 3-methylamino-1-(2-thienyl)propan-1-ol.

2. Description of Related Art 3-methylamino-1-(2-thienyl)propan-1-ol has been shown to be an important intermediate for preparation of (+)-(S)—N-methyl-3-methyl-3-(1-naphthyloxy)-3-(2-thienyl)propylamine oxalate (Duloxetine®), an antidepressant drug. Various methods have been proposed to prepare 3-methylamino-1-(2-thienyl)propan-1-ol. For example, *Chirality*, 12, 26 (2000) discloses a process as shown in the following scheme:

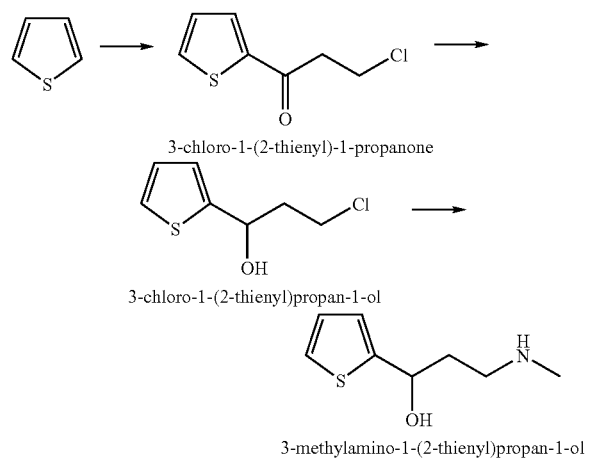

In this example, thiophene is used as the starting material to be acylated by Friedel-Crafts reaction so as to form 3-chloro-1-(2-thienyl)-propanone, then 3-chloro-1-(2-thienyl)-propanone is reduced to 3-chloro-1-(2-thienyl)-propan-1-ol, and 3-chloro-1-(2-thienyl)-propan-1-ol is aminated to form 3-methylamino-1-(2-thienyl)-propan-1-ol with methylamine. In this process, large excess (20 equivalents) of methylamine is required for the amination reaction and the overall yield is low (24%), which renders this process economically less competitive.

U.S. Pat. No. 7,259,264 discloses another process for preparing 3-methylamino-1-(2-thienyl)propan-1-ol as shown in the following scheme:

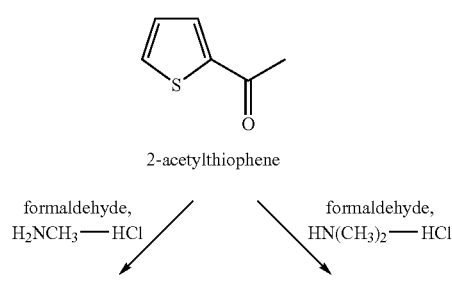

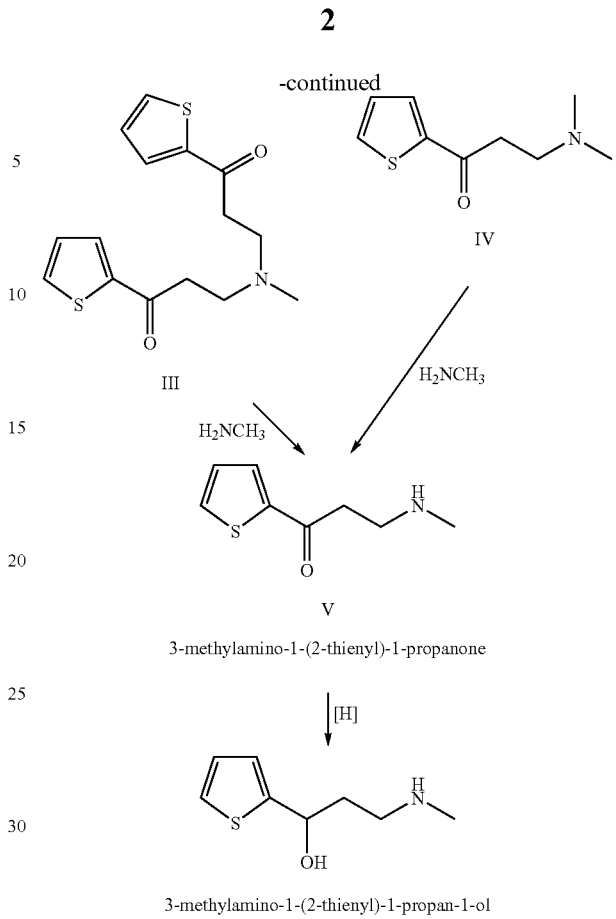

In accordance with U.S. Pat. No. 7,259,264, 3-methylamino-1-(2-thienyl)-propan-1-ol is prepared by reducing an intermediate, 3-methylamino-1-(2-thienyl)-1-propanone (compound V). 2-acetylthiophene is used as the starting material for preparation of 3-methylamino-1-(2-thienyl)-1-propanone (compound V) through diketone (compound III) route or dimethylaminoketone (compound IV) route, and then 3-methylamino-1-(2-thienyl)-1-propanone is reduced to 3-methylamino-1-(2-thienyl)-propan-1-ol. When the above preparation is performed through diketone (compound III) route, large excess (20 equivalents) of methylamine is required, which leads to involvement of complex unit operation of methylamine recycling. Alternatively, when the above preparation is performed through dimethylaminoketone (compound IV) route, large excess (20 equivalents) of methylamine is also required to carry out the amine exchange reaction and the yield is not very high (about 60%). Therefore, the extensive work of purification is required for both routes to prepare 3-methylamino-1-(2-thienyl)-1-propanone (compound V), which leads to higher cost for preparation of 3-methylamino-1-(2-thienyl)propan-1-ol.

Thus, there is a demand for a simple and more efficient process for preparing 3-methylamino-1-(2-thienyl)propan-1-ol with higher yield and lower cost.

SUMMARY OF THE INVENTION

In light of the above-mentioned drawbacks of the prior art, a primary objective of the present invention is to provide a novel methylhydroxylaminopropanol compound as an intermediate for preparation of 3-methylamino-1-(2-thienyl)propan-1-ol.

It is another objective of the present invention to provide a process for preparing 3-methylamino-1-(2-thienyl)propan-1-ol with higher yield and lower cost.

To achieve the above-mentioned and other objectives, the process for preparing 3-methylamino-1-(2-thienyl)-propan-1-ol of the present invention includes steps of: (i) performing a Mannich reaction of 2-acetylthiophene, formaldehyde and a methylhydroxylamine of formula, HNCH$_3$(OR), to form a substituted amino ketone of formula (I) shown in the following scheme; (ii) reducing the substituted amino ketone of formula (I) to form a methylhydroxylaminopropanol compound of formula (II) shown in the following scheme; and (iii) performing an N,O-cleavage reaction of the methylhydroxylaminopropanol compound of formula (II) to form 3-methylamino-1-(2-thienyl)-propan-1-ol;

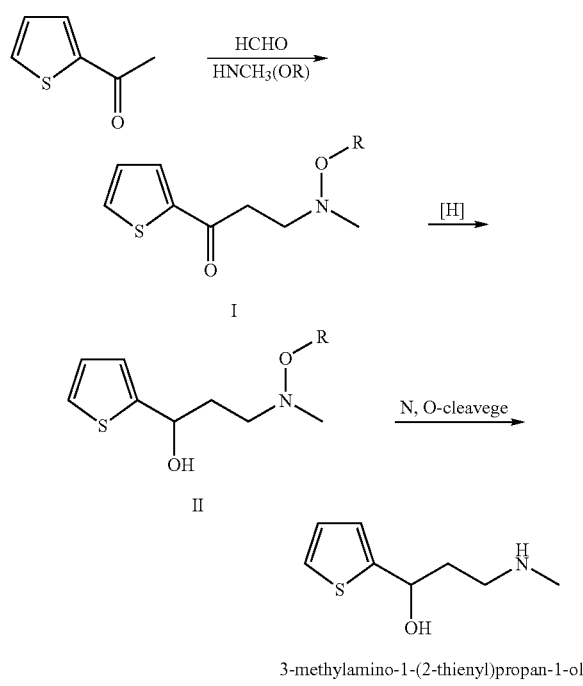

wherein R is a hydrogen atom, an alkyl group having 1 to 8 carbon atoms or an aryl group having 6 to 10 carbon atoms,

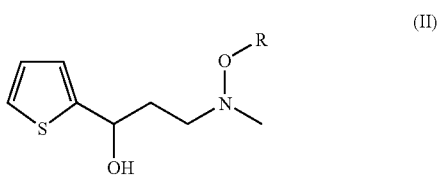

wherein R is a hydrogen atom, an alkyl group having 1 to 8 carbon atoms or an aryl group having 6 to 10 carbon atoms.

DETAILED DESCRIPTION OF PREFERRED EMBODIMENTS

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

The present invention provides a novel methylhydroxylaminopropanol compound of formula (II), either in racemic or optical active form:

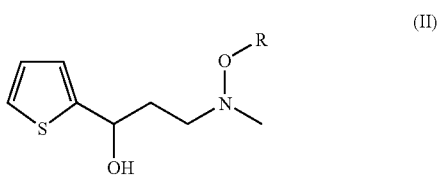

wherein R is a hydrogen atom, an alkyl group having 1 to 8 carbon atoms or an aryl group having 6 to 10 carbon atoms.

R in the above formula (II) is preferably an alkyl group having 1 to 4 carbon atoms, and is more preferably a methyl group.

In addition, the present invention provides the use of methylhydroxylaminopropanol compounds of formula (II) as an intermediate for preparation of 3-methylamino-1-(2-thienyl)propan-1-ol. It is known that 3-methylamino-1-(2-thienyl)propan-1-ol is an important intermediate for preparation of (+)-(S)—N-methyl-3-methyl-3-(1-naphthyloxy)-3-(2-thienyl)propylamine oxalate (Duloxetine®), which is an antidepressant drug.

Furthermore, the present invention provides a process for preparing 3-methylamino-1-(2-thienyl)-propan-1-ol, wherein the methylhydroxylaminopropanol compound of formula (II) is used as an intermediate. The process of the present invention is summarized in Scheme 1.

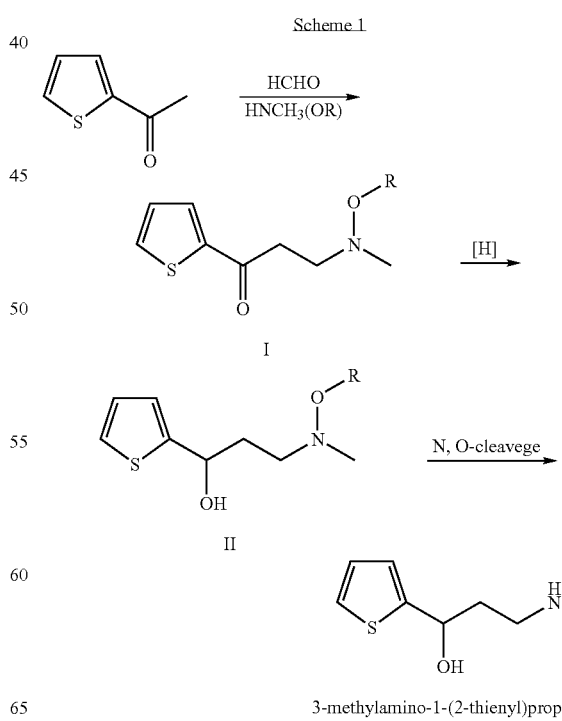

In Scheme 1, R is a hydrogen atom, an alkyl group having 1 to 8 carbon atoms or an aryl group having 6 to 10 carbon atoms.

In more detail, the process of the present invention includes steps of:

(i) performing a Mannich reaction of 2-acetylthiophene, formaldehyde and a methylhydroxylamine of formula, $HNCH_3(OR)$, to form a substituted amino ketone of formula (I);

(ii) reducing the substituted amino ketone of formula (I) to a methylhydroxylaminopropanol compound of formula (II); and (iii) performing an N,O-cleavage reaction of methylhydroxylaminopropanol compound of formula (II) to form 3-methylamino-1-(2-thienyl)-propan-1-ol.

The step (i) of the process is carried out at a temperature ranged from 90° C. to 15° C., preferably 80° C. to 40° C., and more preferably 70° C. to 50° C. The substituted amino ketone of formula (I) obtained in the step (i) is either as a free form or as an acid addition salt.

The reduction of the substituted amino ketone of formula (I) in the step (ii) is performed by traditional or chiral reduction, and either a racemic form or an optically active form of the methylhydroxylaminopropanol compound of formula (II) is obtained. The optically active form can be obtained enzymatically or chemically, for example, by conventional enantioselective hydrogenation or by the methods using borane, $NaBH_4$ or $LiAlH_4$ as a reducing agent with chiral ligands.

In one preferred embodiment, reduction of the substituted amino ketone of formula (I) in the step (ii) is carried out in a mixture of water and an alcohol such as methanol, in the presence of a reducing agent such as sodium borohydride ($NaBH_4$). The reaction mixture is adjusted to pH of 6 to 14, preferably 11, by addition of a base such as NaOH, and stirred for 0.5 to 2 hours, preferably 1 hour.

The N,O-cleavage reaction of the methylhydroxylaminopropanol compound of formula (II) in the step (iii) of the process is carried out by hydrogenation in the presence of a catalyst such as Raney-nickel, or by chemical reduction methods such as those using $LiAlH_4$ or zinc metal as reducing agent.

In one preferred embodiment, the methylhydroxylaminopropanol compound of formula (II) is hydrogenated in methanol in the presence of Raney-nickel at a temperature ranged from 80° C. to 15° C., preferably 70° C. to 40° C., for 9 to 15 hours.

Compared with the conventional process, 3-methylamino-1-(2-thienyl)-propan-1-ol can be obtained with higher yield and lower cost from the process of the present invention.

EXAMPLES

Step 1

Synthesis of
3-methoxymethylamino-1-(2-thienyl)-1-propanone hydrochloride salt

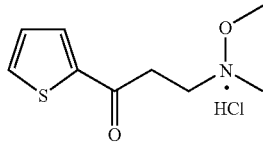

27.7 g of N,O-dimethylhydroxylamine hydrochloride, 9.3 g of paraformaldehyde, 6.4 g of 32% hydrochloride, 30.0 g of 2-acetylthiophene and 100 g of isopropanol were provided into a flask. After being stirred at 60° C. for 13 hours, the reaction mixture was cool down to room temperature. The crystal thus formed was filtered, washed with 30 g of isopropanol and dried under reduced pressure to obtain 42.5 g of 3-methoxymethylamino-1-(2-thienyl)-1-propanone hydrochloride salt (75.9%). $^1H$ NMR (400 MHz, $CDCl_3$) δ (ppm)=3.1 (s, 3H), 3.7-3.8 (br, 4H), 4.1 (s, 3H), 7.2 (t, J=4.5 Hz, 1H), 7.7 (d, J=4.9 Hz, 1H), 7.9 (d, J=3.5 Hz, 1H).

Step 2

Synthesis of
3-methoxymethylamino-1-(2-thienyl)propan-1-ol

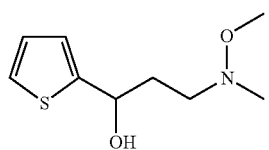

38.6 g of 3-methoxymethylamino-1-(2-thienyl)-1-propanone hydrochloride salt obtained in Step 1 was dissolved in 115 g of methanol and 40 g of water. The pH value of the resulting solution was adjusted to 11 by addition of 45% NaOH. 2.5 g of sodium borohydride was added, and the mixture was stirred for 1 hour. Afterward the reaction mixture was filtered, concentrated and extracted with 80 g of toluene. The organic layer was concentrated to obtain 33.8 g of 3-methoxymethylamino-1-(2-thienyl)propan-1-ol as an oily product. $^1H$ NMR (400 MHz, $CDCl_3$) δ (ppm)=3.0 (s, 3H), 3.0-3.1 (m, 1H), 4.1 (s, 3H), 4.0-4.1 (m, 3H), 6.1 (dt, J=7.4, 15.4 Hz, 1H), 6.9 (d, J=15.7 Hz, 1H), 7.0 (dd, J=3.7, 5.0 Hz, 1H), 7.1 (d, J=3.4 Hz, 1H).

Step 3

Synthesis of
3-methylamino-1-(2-thienyl)propan-1-ol

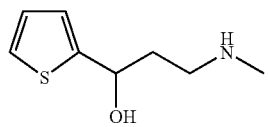

3-methoxymethylamino-1-(2-thienyl)propan-1-ol obtained in Step 2 was dissolved in 60 g of methanol and 3.3 g of Raney-Nickel were provided in a glass autoclave. The resulting solution was hydrogenated at 50° C. for 12 hours. Upon completion of hydrogenation, the reaction mixture was filtered, and the solvent was removed under reduced pressure to obtain 3-methylamino-1-(2-thienyl)propan-1-ol as a crystal (yield: 26.5 g, 91.5% from Example 2).

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. A methylhydroxylaminopropanol compound of formula (II) in racemic or optical active form, or acid addition salts thereof:

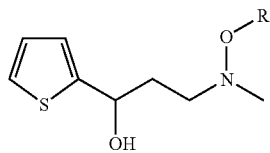

(II)

wherein R is an alkyl group having 1 to 8 carbon atoms or an aryl group having 6 to 10 carbon atoms.

2. The methylhydroxylaminopropanol compound of formula (II) according to claim 1, wherein R is an alkyl group having 1 to 4 carbon atoms.

3. The methylhydroxylaminopropanol compound of formula (II) according to claim 2, wherein R is methyl group.

4. The methylhydroxylaminopropanol compound of formula (II) according to claim 1, which is used as an intermediate in synthesis of 3-methylamino-1-(2-thienyl)propan-1-ol.

5. The methylhydroxylaminopropanol compound of formula (II) according to claim 4, wherein 3-methylamino-1-(2-thienyl)-propan-1-ol is an intermediate for preparation of (+)-(S)—N-methyl-3-methyl-3-(1-naphthyloxy)-3-(2-thienyl)propylamine oxalate.

6. A process for preparing 3-methylamino-1-(2-thienyl)-propan-1-ol, comprising the steps of:
(i) performing a Mannich reaction of 2-acetylthiophene, formaldehyde and a methylhydroxylamine of formula, HNCH$_3$(OR), to form a substituted amino ketone of formula (I) shown in the following scheme;
(ii) reducing the substituted amino ketone of formula (I) to form a methylhydroxylaminopropanol compound of formula (II) shown in the following scheme; and
(iii) performing an N,O-cleavage reaction of the methylhydroxylaminopropanol compound of formula (II) to form 3-methylamino-1-(2-thienyl)-propan-1-ol;

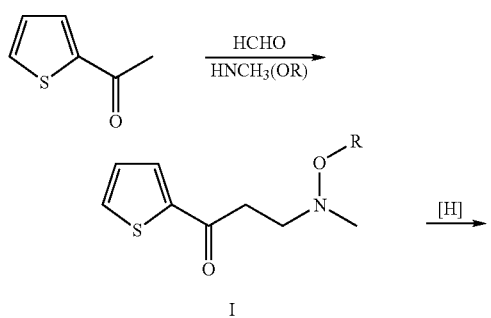

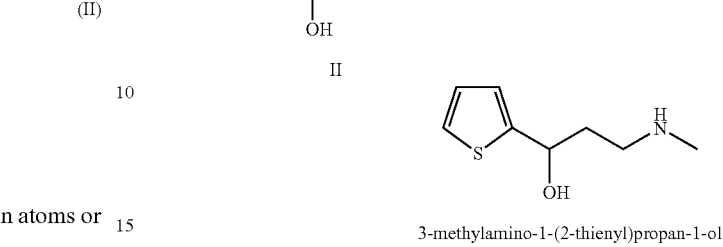

3-methylamino-1-(2-thienyl)propan-1-ol wherein R an alkyl group having 1 to 8 carbon atoms or an aryl group having 6 to 10 carbon atoms.

7. The process according to claim 6, wherein the substituted amino ketone of formula (I) obtained in the step (i) is as a free form or as an acid addition salt.

8. The process according to claim 6, wherein the step (ii) is performed by traditional or chiral reduction.

9. The process according to claim 6, wherein the methylhydroxylaminopropanol compound of formula (II) is in a racemic form or an optically active form.

10. The process according to claim 6, wherein the N,O-cleavage reaction of the methylhydroxylaminopropanol compound of formula (II) in the step (iii) is carried out by hydrogenation in an alcohol in the presence of Raney-nickel at a temperature ranging from 80° C. to 15° C.

11. The process according to claim 6, wherein the N,O-cleavage reaction of the methylhydroxylaminopropanol compound of formula (II) in the step (iii) is carried out by a chemical reduction using LiAlH$_4$ or zinc metal as a reducing agent.

12. The process according to claim 6, wherein the step (i) is performed at a temperature ranging from 90° C. to 15° C.

13. The process according to claim 6, wherein the step (ii) is performed at a pH value ranging from 6 to 14.

14. A process for preparing the methylhydroxylaminopropanol compound of formula (II) according to claim 1, comprising the steps of:
(i) performing a Mannich reaction of 2-acetylthiophene, formaldehyde and a methylhydroxylamine of formula HNCH$_3$(OR) to form a substituted amino ketone of formula (I); and
(ii) reducing the substituted amino ketone of formula (I) to form the methylhydroxylaminopropanol compound of formula (II).

15. The process according to claim 14, wherein the step (i) is performed at a temperature ranging from 90° C. to 15° C.

16. The process according to claim 14, wherein the step (ii) is performed at pH value ranging from 6 to 14.

* * * * *